US012558227B2

(12) United States Patent
Chudik

(10) Patent No.: US 12,558,227 B2
(45) Date of Patent: Feb. 24, 2026

(54) HUMERAL IMPLANT AND METHOD

(71) Applicant: Steven C. Chudik, Western Springs, IL (US)

(72) Inventor: Steven C. Chudik, Western Springs, IL (US)

( * ) Notice: Subject to any disclaimer, the term of this patent is extended or adjusted under 35 U.S.C. 154(b) by 0 days.

(21) Appl. No.: 17/532,714

(22) Filed: Nov. 22, 2021

(65) Prior Publication Data

US 2023/0157832 A1 May 25, 2023

(51) Int. Cl.
    *A61F 2/40*       (2006.01)
    *A61F 2/30*       (2006.01)
    *A61F 2/46*       (2006.01)

(52) U.S. Cl.
    CPC ........ *A61F 2/4003* (2013.01); *A61F 2/30749* (2013.01); *A61F 2/4612* (2013.01); *A61F 2002/3006* (2013.01); *A61F 2002/30235* (2013.01); *A61F 2002/30433* (2013.01); *A61F 2002/30932* (2013.01); *A61F 2002/4022* (2013.01); *A61F 2002/4051* (2013.01)

(58) Field of Classification Search
    CPC .. A61F 2/4003; A61F 2/30749; A61F 2/4612; A61F 2002/3006; A61F 2002/30235; A61F 2002/30433; A61F 2002/4022; A61F 2002/4051; A61F 2002/30332; A61F 2002/30405; A61F 2002/30507; A61F 2002/30616; A61F 2002/30878; A61F 2002/30884; A61F 2/4014; A61F 2002/30604; A61F 2002/4018; A61F 2002/4062; A61F 2/40; A61F 2/4059; A61F 2/4081
See application file for complete search history.

(56) References Cited

U.S. PATENT DOCUMENTS

| | | | | |
|---|---|---|---|---|
| 4,752,296 | A | * 6/1988 | Buechel | .................... A61F 2/40 |
| | | | | 623/23.14 |
| 4,904,263 | A | * 2/1990 | Buechel | .................... A61F 2/36 |
| | | | | 623/23.44 |
| 5,593,445 | A | 1/1997 | Waits | |
| 9,364,333 | B1 | * 6/2016 | Paulos | ............... A61B 17/1684 |
| 9,445,910 | B2 | 9/2016 | Chudik | |
| 9,968,459 | B2 | 5/2018 | Chudik | |
| 2001/0014828 | A1 | * 8/2001 | Yoon | .................... A61F 2/30907 |
| | | | | 623/23.46 |
| 2003/0078670 | A1 | * 4/2003 | Grimes | ................. A61F 2/3601 |
| | | | | 623/23.21 |
| 2005/0043805 | A1 | * 2/2005 | Chudik | .............. A61B 17/1684 |
| | | | | 623/908 |

(Continued)

OTHER PUBLICATIONS

Preliminary clinical and radiographic results with the Fixion intramedullary nail: an inflatable self-locking system for long bone fractures, J. Orthopaed Traumatol 3:135-140 (2001).

*Primary Examiner* — Brian A Dukert
(74) *Attorney, Agent, or Firm* — Erickson Law Group, PC.

(57) ABSTRACT

A humeral implant is disclosed. The implant has a humeral surface component and a stem. The humeral surface component has an articular surface and is configured for fixation to an articular portion of a proximal humerus. The stem is configured for post-surgery axial movement within the humerus. The stem is connected to the humeral surface component opposite of the articular surface. A method of implanting a humeral implant is also disclosed.

17 Claims, 26 Drawing Sheets

(56) References Cited

U.S. PATENT DOCUMENTS

2010/0174346 A1 * 7/2010 Boyden ..................... A61F 2/30
                                                             607/113
2013/0289738 A1 * 10/2013 Humphrey ................ A61F 2/30
                                                             623/23.42

* cited by examiner

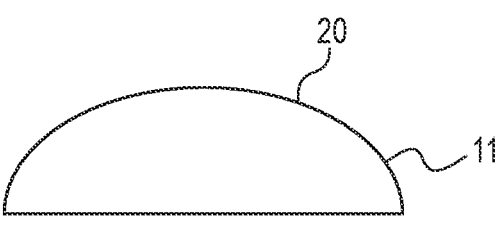
FIG. 3C
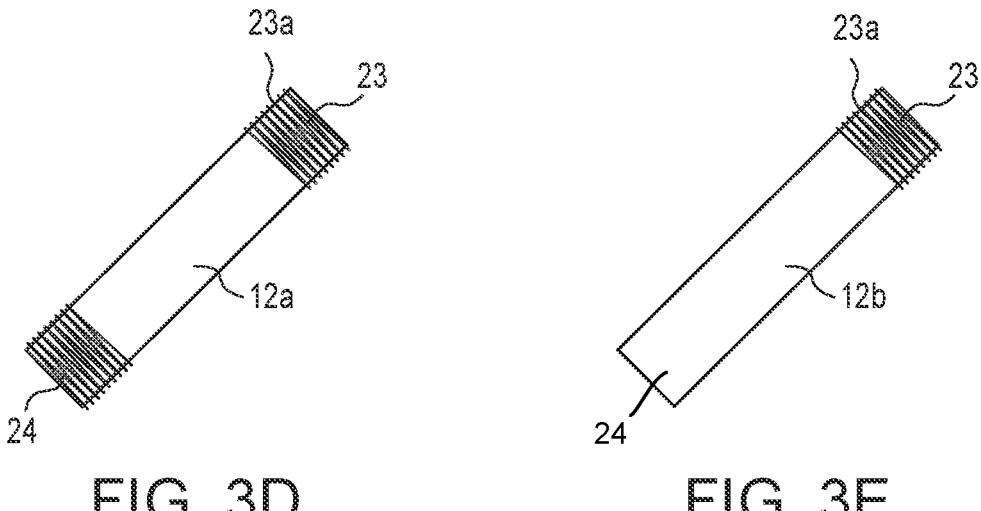
FIG. 3D                    FIG. 3E
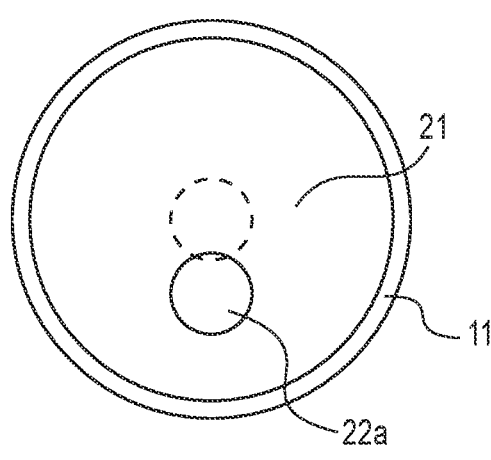
FIG. 4

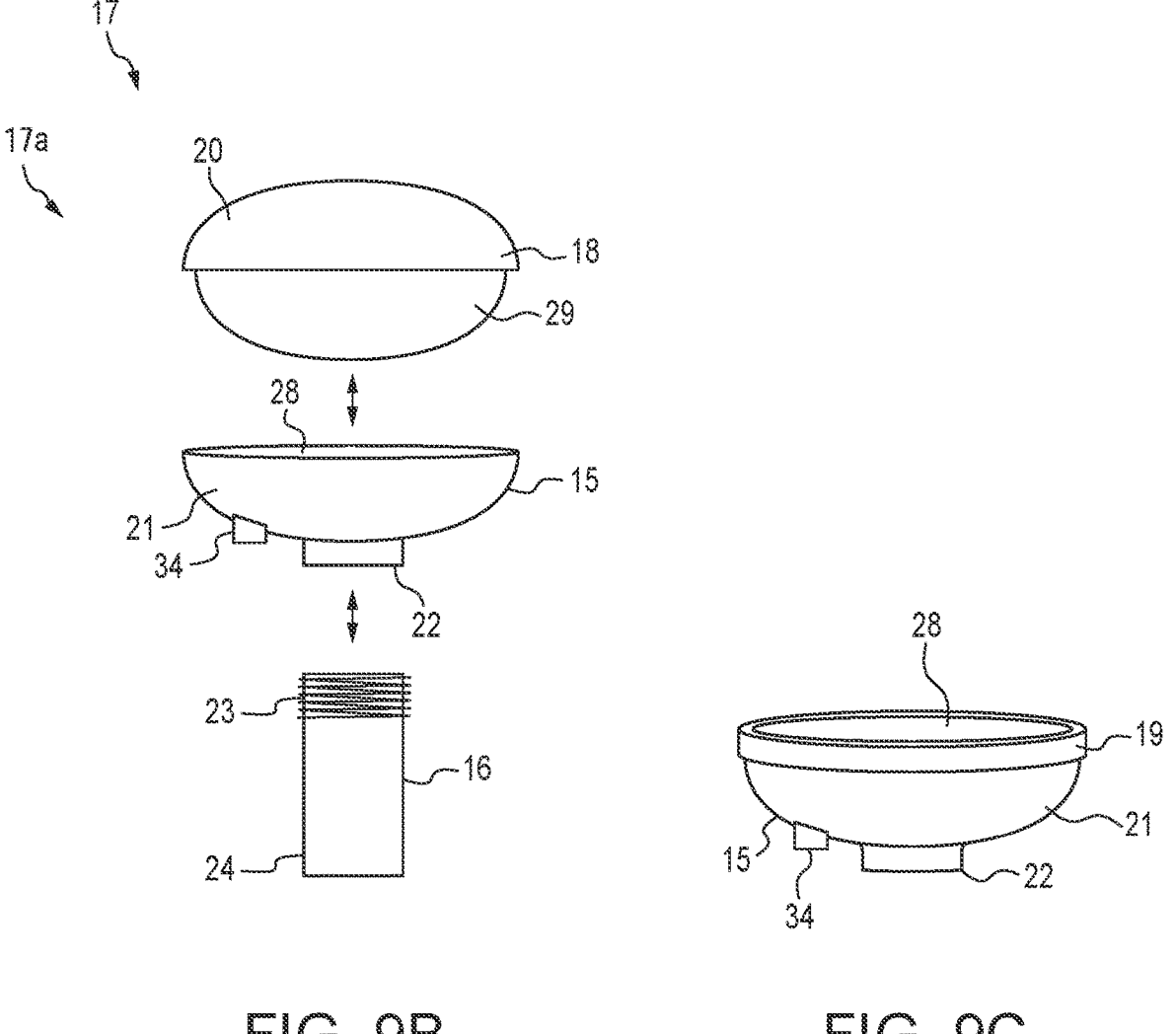
FIG. 9B                    FIG. 9C

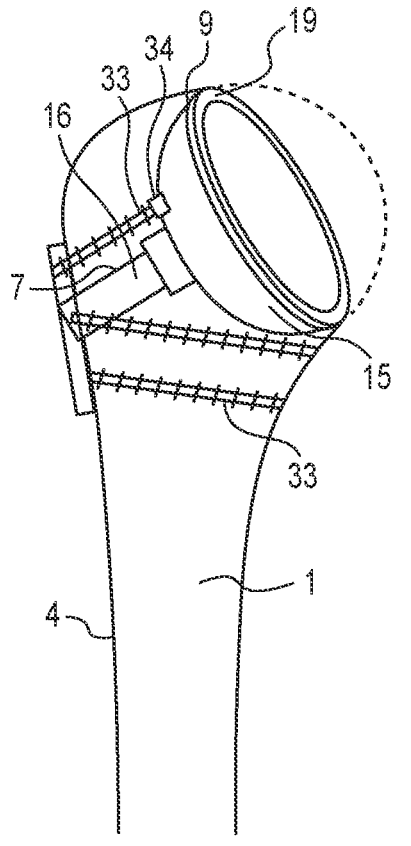
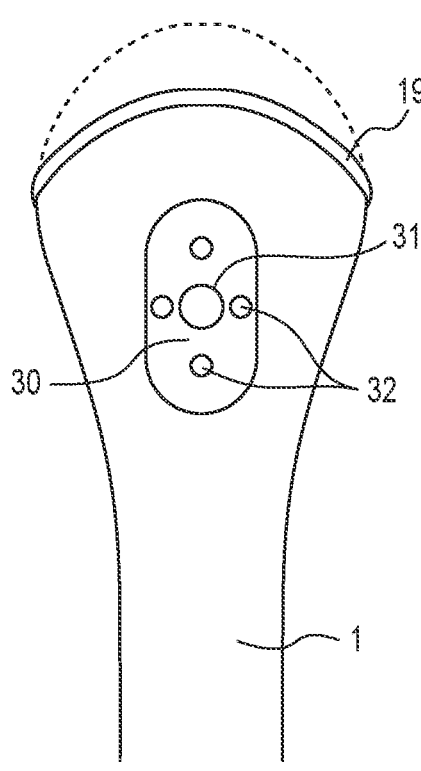
FIG. 10A                     FIG. 10B

HUMERAL IMPLANT AND METHOD

FIELD OF THE INVENTION

The present invention relates in general to humeral implants.

BACKGROUND OF THE INVENTION

Orthopaedic surgeons often perform joint replacement surgery on patients who suffer pain and physical limitations caused by joint surfaces which have degenerative, traumatic, or other pathologic damage. The success of replacement surgery is related to the degree of morbidity associated with the surgical technique and also to the ability of the surgery to restore the natural anatomy and biomechanics of the joint. The present inventor recognized the need for improved rates of surgical success through an improved implant and method.

BRIEF SUMMARY OF THE INVENTION

A new humeral implant is disclosed. The implant has a humeral surface component and a stem. The humeral surface component has an articular surface and is configured for fixation to an articular portion of a proximal humerus. The stem is configured for post-surgery axial movement within the humerus. The stem is connected to the humeral surface component opposite of the articular surface.

Accordingly, one aspect of the present invention is to provide a novel humeral implant for shoulder replacement surgery that can be implemented with conventional, minimally invasive, or novel surgical techniques.

Another aspect of the present invention is to provide a humeral implant which includes an articular surface component with anatomic geometry with different radii of curvature in the axial and coronal planes.

Another aspect of the present invention is to provide a humeral implant which includes a stem that resides along a central axis of the proximal humerus rather than in the intramedullary canal.

Another aspect of the present invention is to provide a humeral implant that partially resurfaces the humeral head.

Another aspect of the present invention is to provide a humeral implant which obtains durable fixation on the subchondral bone of an anatomic head.

Another aspect of the present invention is to provide a humeral implant which obtains durable fixation with the non-articular lateral humeral cortex.

Another aspect of the present invention is to provide a humeral implant which obtains slidable engagement with a tunnel along a central axis of the humerus.

Another aspect of the present invention is to provide a humeral implant which obtains slidable engagement with the non-articular lateral humeral cortex.

Another aspect of the present invention is to provide a humeral implant which preserves humeral bone stock and allows increased physiologic load transmission from the joint surface in a patient's shoulder along the bone of the proximal humerus.

Another aspect of the present invention is to provide a humeral implant which has an interchangeable articular component and allows conversion between an anatomic shoulder arthroplasty and a reverse shoulder arthroplasty.

Another aspect of the present invention is to provide a modular bone reamer-which can be used with traditional open and transhumeral minimally invasive techniques for shoulder arthroplasty.

Another aspect of the present invention is to provide a modular bone reamer which can be used to prepare a humerus and a glenoid process in a shoulder joint without transecting their rotator cuff tendon and without dislocating their shoulder joint.

Another aspect of the present invention is to provide a modular bone reamer which can be used to prepare a humerus and a glenoid process in a shoulder joint perpendicularly to the shaft of the reamer.

A method of implanting a humeral implant is disclosed, comprising: fixing an articular humeral component comprising an articular surface to a prepared articular portion of a proximal humerus, placing a stem in a tunnel in the proximal humerus without fixing the stem within the tunnel against post-surgery longitudinal movement; and, connecting the stem to the articular humeral component.

Other features and advantages of this invention will be apparent to orthopaedic surgeons and other persons who are skilled in the art of shoulder repair and reconstruction, particularly after reviewing the following detailed description of the invention and the embodiments thereof, from the claims, and from the accompanying drawings.

BRIEF DESCRIPTION OF THE DRAWINGS

FIG. 3C is a side view of a side of the articular humeral component of the humeral implant of FIG. 3A.

FIG. 3D is a side view of a first embodiment stem for the humeral implant of FIG. 3A configured for fixed engagement of the implant with the humeral bone.

FIG. 3E is a side view of a second embodiment stem for the humeral implant of FIG. 3A configured for slidable engagement in the humeral bone.

FIG. 4 is a bottom view of a second embodiment of the articular humeral component of a second embodiment humeral implant of the invention having an offset coupling device for a stem.

FIG. 9B is an exploded side perspective view of the assembly of the convertible humeral implant of FIG. 8.

FIG. 9C is a side perspective view of the shell of the convertible humeral implant of FIGS. 7 and 8 with a peripheral rim and fin(s) to resist subsidence and rotation respectively.

FIG. 10A is a perspective view of an ingrowth shell of the convertible humeral implant of FIG. 7 positioned in a prepared humerus bone with an associated lateral buttress washer-plate secured to the bone with screws engaging the implant with a stem.

FIG. 10B is a second perspective view of the ingrowth shell of FIG. 10A.

DETAILED DESCRIPTION OF THE INVENTION

Figure 1A:
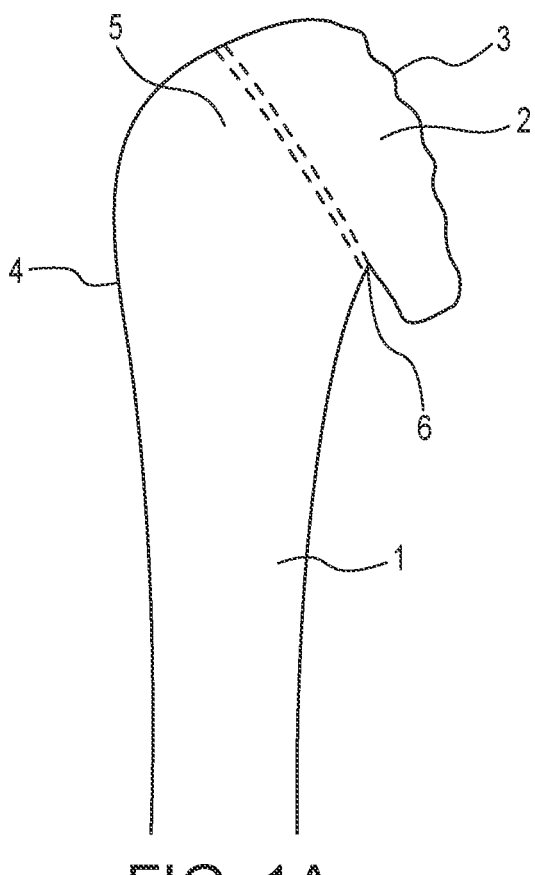
FIG. 1A is a perspective view of a portion of a humerus bone with a common arthritic deformity of the humeral head.
Figure 1B:
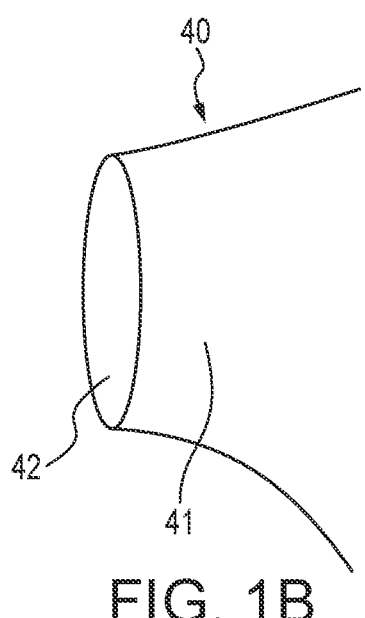
FIG. 1B is a perspective view of a portion of a scapula bone with a glenoid process.

Shoulder arthroplasty surgery traditionally requires transection of the subscapularis tendon, dislocation of the shoulder joint and resection of the head 2 of the humerus bone 1 at the level of plane 6 of the anatomic neck (FIG. 1A) to gain sufficient access to prepare and resurface the glenoid 40 (FIG. 1B). Using a novel transhumeral method allows for proper access to the glenoid 40 while sparing the subscapularis tendon and avoiding dislocation and aggressive resection of humeral head bone 2. Novel humeral implants 10, 13, 17 (FIGS. 2A, 5, 6A, 6B, 7, 8, 9A, 9B, 10A, 10B) are usable with this novel transhumeral method, which provides a minimally invasive technique, but can also be used with traditional surgical techniques.

Figure 2A:
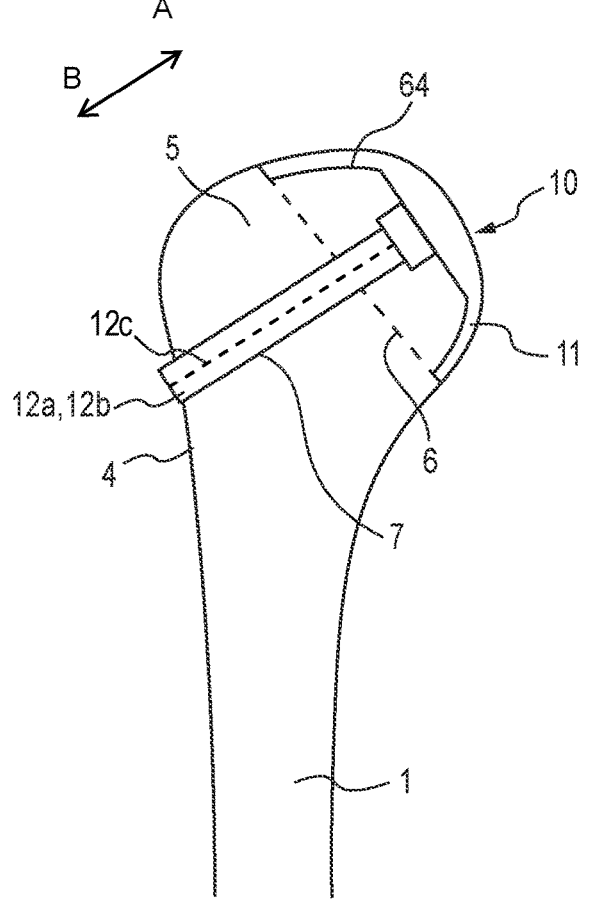
FIG. 2A is a side, partially transparent, view of a humeral implant of the invention utilizing a stem as described herein in position on a prepared humerus bone.
Figure 2B:
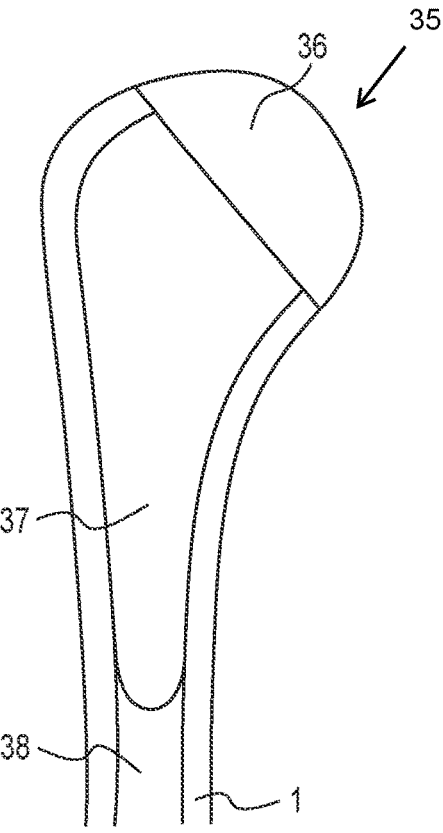
FIG. 2B is a side section view of a traditional humeral implant positioned in a prepared humerus bone.

In the novel transhumeral method, the components of the new humeral implants 10, 13, 17 can be inserted without cutting the rotator cuff nor dislocating the shoulder joint through non-bony soft-tissue passageways with or without the assistance of transhumeral tunnel 7 to the shoulder. The novel humeral implants 10, 13,17 avoid the limitations associated with traditional humeral implants 35 having round, not oval shaped, articular components 36 with offset intramedullary canal stems 37 designed to be fit in the intramedullary canal 38 of the humerus 1 (FIG. 2B). Limitations associated with traditional humeral implants 35 include but are not limited to aggressive humeral bone resection, complicated implant removal, and difficulty in obtaining anatomic parameters of humeral version, height, depth, inclination, and radius of curvature.

Figure 2C:
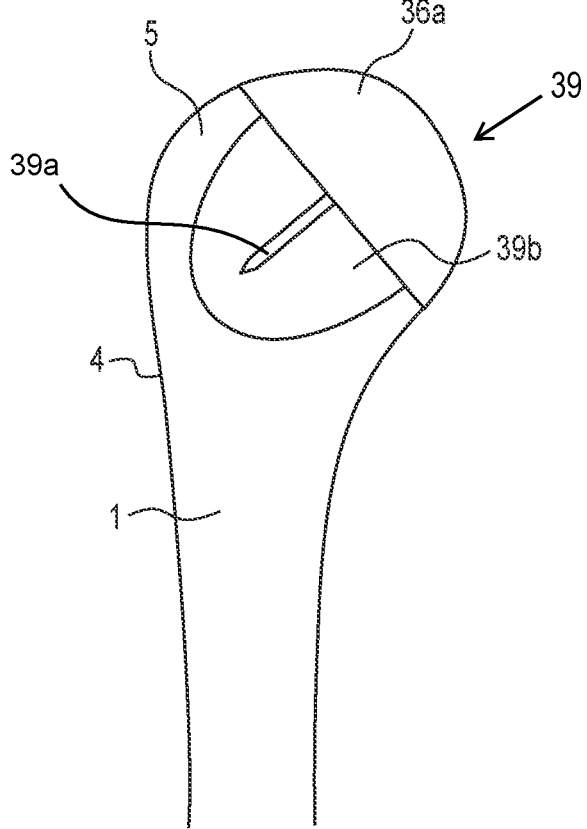
FIG. 2C is a side, partially transparent, view of another common humeral implant utilizing fins in a metaphyseal position of a prepared humerus bone.
Figure 13A:
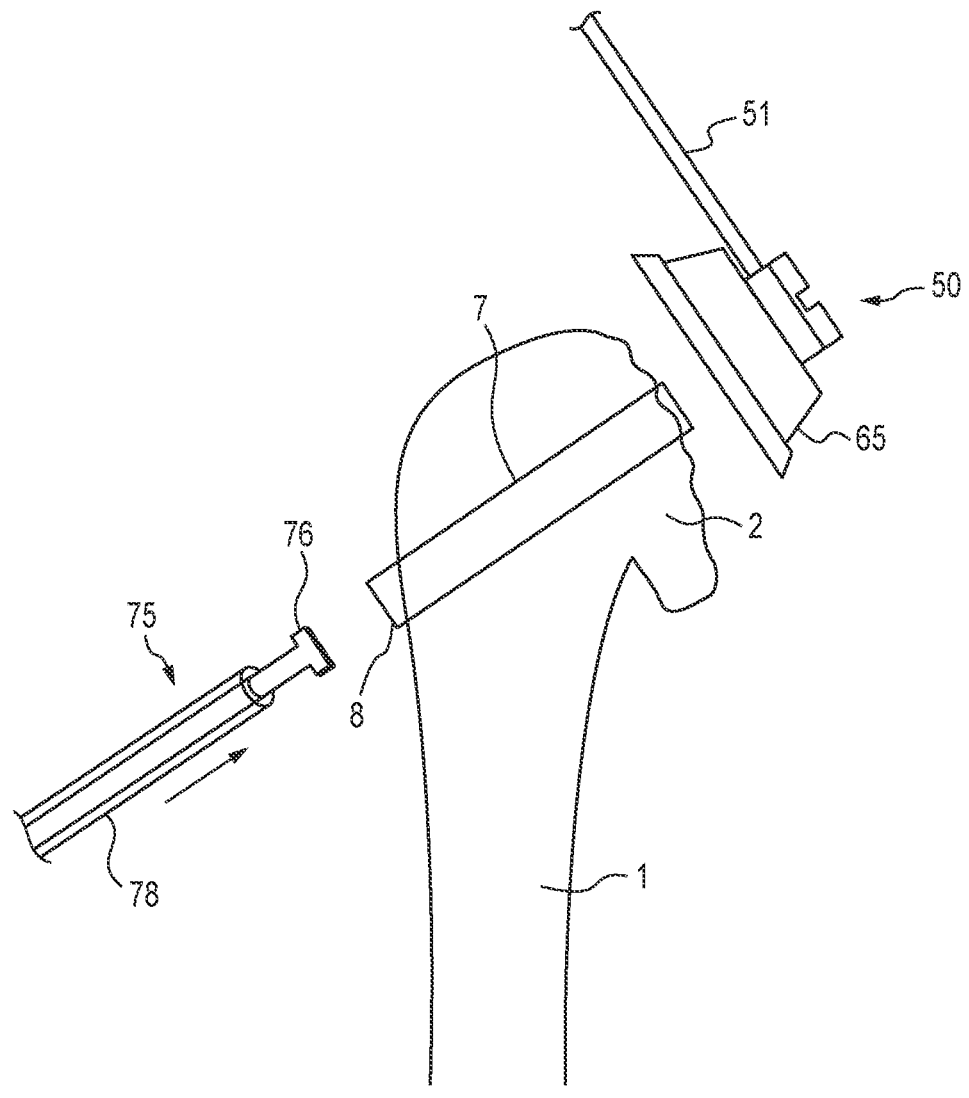
FIG. 13A is a perspective view of the humeral reamer and shaft of FIG. 12A arranged through a transhumeral passage in the humerus to prepare a humerus for the installation of the new humeral implant.
Figure 13B:
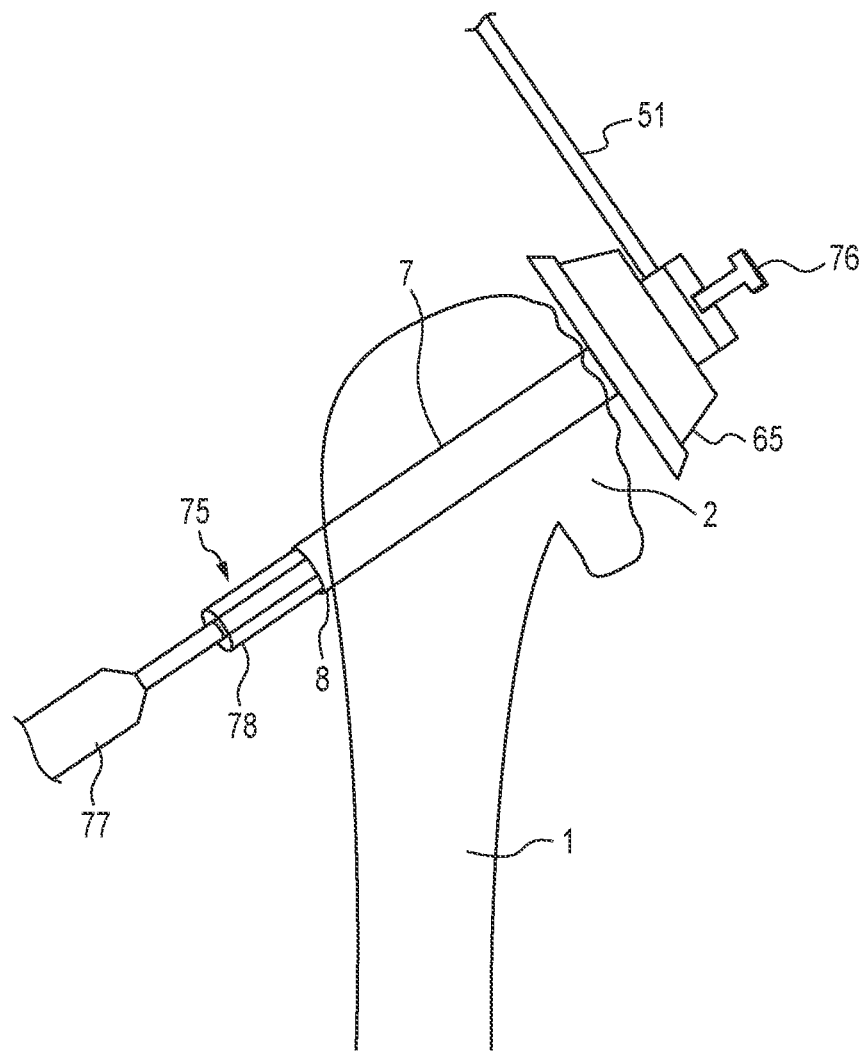
FIG. 13B is a perspective view of the humeral reamer and shaft of FIG. 13A arranged through a transhumeral passage in the humerus for a second step to prepare a humerus for the installation of the new humeral implant.
Figure 13C:
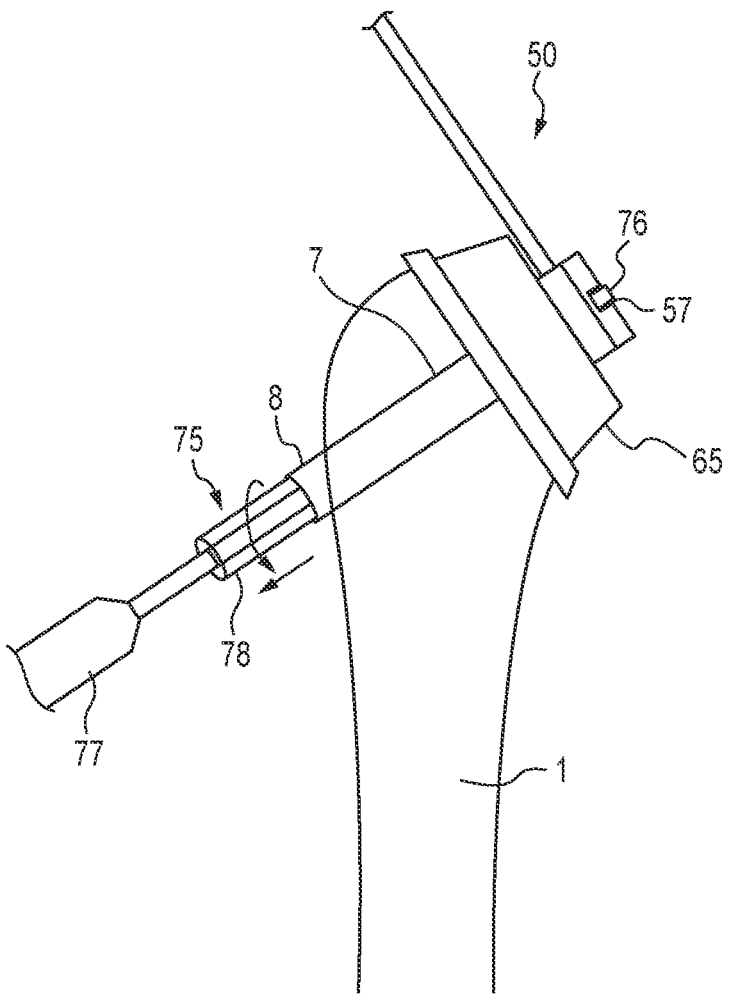
FIG. 13C is a perspective view of the humeral reamer and shaft of 13A arranged through a transhumeral passage in the humerus for a third step to prepare a humerus for the installation of the new humeral implant.
Figure 13D:
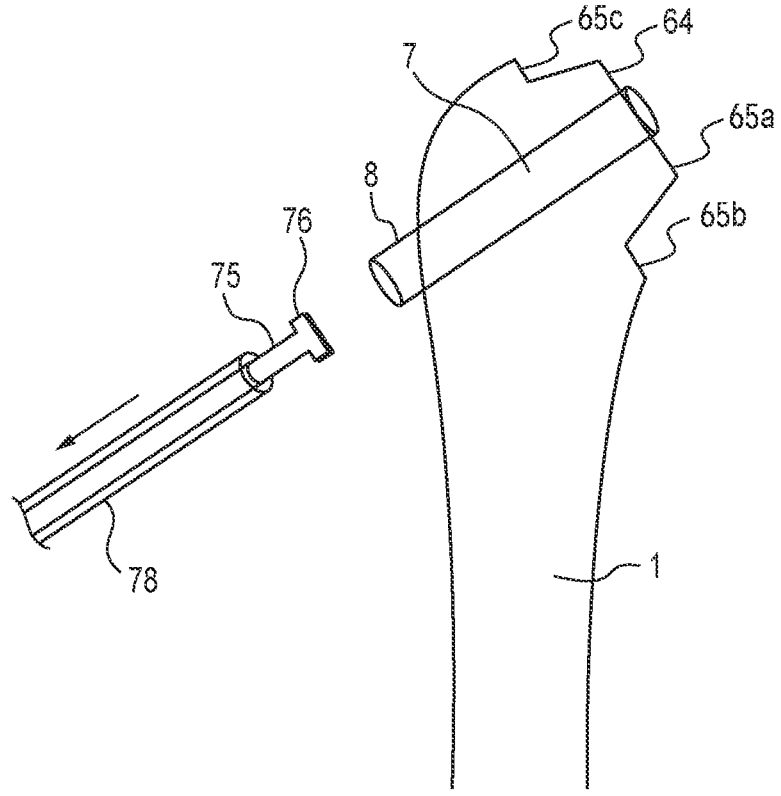
FIG. 13D is a perspective view of the prepared humerus and transhumeral sheath after a fourth step to prepare the humerus for the installation of the new humeral implant where the reamer shaft and head of FIG. 13A are disengaged and removed.

The novel humeral implant 10 also has improvements over other humeral implants 39 fixed in the humeral metaphysis bone 5 (FIG. 2C). The humeral implant 39 has a round articular surfaces 36a and intersecting elongated fins 39a, 39b extending from the component comprising the surface 36a. The novel humeral implant 10 is improved over implant 39, at least in that the novel implant utilizes the native dense articular surface 3 and its subchondral bone 64 and non-articular lateral bony cortex 4 of the humerus for improved bony fixation and support of the implant (FIG. 2A). The dense articular surface 3 comprises a thickness. Therefore, even when the humeral head bone 2 is prepared, such as shown in FIGS. 2A and 13D, to receive the novel implant at least a portion of the articular surface 3 is often retained after such preparation and thereby provides support for the implant.

The novel humeral implant 10 also allows for easier removal and bone preservation during revision surgery. New humeral implants 13, 17 (FIGS. 7, 8) also allow convertibility not afforded by prior art implants, such as implant 39. In some embodiments, the novel humeral implant 10 has a smaller articular humeral component 26, having a smaller humeral articulating surface 20a, and only partially resurfaces the worn and damaged humeral articular surface 3 (FIG. 5), as compared to the articular humeral component 11 and articulating surface 20 of FIG. 2A.

The novel humeral implant 10 preserves the dense quality bone of the anatomic head 2 and comprises a removably attached stem 12a, 12b which does not reside in nor rely on the intramedullary canal 38 for fixation (FIGS. 2A, 3D, 3E, 5). In some embodiment, the implant 10 is modular at least in that the stem is connectable to the articular humeral component 11. The implant 10 obtains stability from contact with good quality bone from the anatomic head 2 and non-articular lateral bony cortex 4 of the humerus 1. The stem 12a, 12b is positioned in a transhumeral tunnel 7 along a central axis of the humeral metaphysis 5 allowing for the use of articular humeral components 11, 26 each with a smooth articulating surface 20. In some embodiments, the articulating surface comprises variable more anatomic anterior-to-posterior and superior-to-inferior radii of curvature (FIGS. 3A, 3B, 3C, 3D, 3E, 4).

Figure 3A:
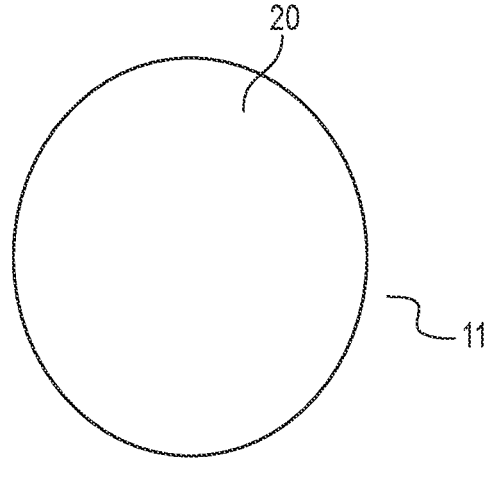
FIG. 3A is a top view of the articular humeral component of the humeral implant of FIG. 2A disclosing the implant's elliptical shape which incorporates varying radii of curvature.
Figure 3B:
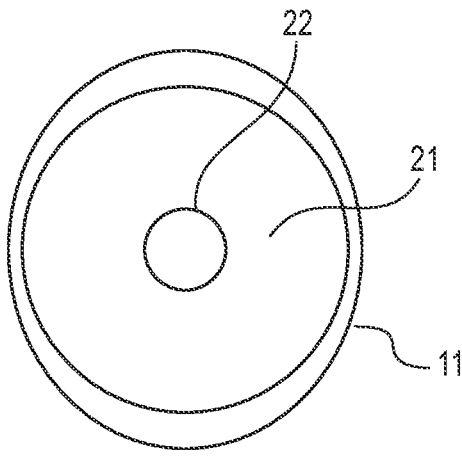
FIG. 3B is a bottom view of the articular humeral component of the humeral implant of FIG. 3A disclosing its bone ingrowth surface and disposition of a coupling device for engaging an associated stem for the implant.

In some embodiments, the underside of the articular humeral components 11, 26 has a bony ingrowth surface 21 and/or other bone adherent features. In some embodiments, the articular humeral component 11 can also have a central coupling site 22 or off-center coupling site 22a for the stem 12a, 12b (FIGS. 3B and 4).

In some embodiments, the novel humeral implants 10, 13, 17 comprise a stem 12a, 12b, 16 that provides slidable engagement with the bone of the humeral metaphysis 5 and/or non-articular lateral bony cortex 4 of the humerus 1 which allows for more physiologic loading of the humeral bone 1, 2, 3, 5 than with traditional humeral implants 35 and humeral implants 39. Additionally, in the case of a periprosthetic humeral fracture complication, the design of the new humeral implants 10, 13, 17 will provide for a pattern of proximal humeral fracture at the end of the unfixed stem, more easily managed than those predicted to occur with traditional humeral implants 35 and humeral implants 39 and which does not compromise implant fixation.

The worn articular surface 3 of the humerus 1 can be prepared with a modular transhumeral reamer 50, 80 (FIGS. 11A, 11B, 11C, 11D, 11E, 12A, 12B, 13A, 13B, 13C, 13D, 14A, 14B, 14C, 14D). The modular transhumeral reamer 50, 80 has a transhumeral reamer shaft 75 and modular cutting reamer head 65, 81 with an attached handle 51 that still allows the reamer head 65, 81 to spin around its central axle 55 in the ring end 52 while it is held in position by the handle 51. In one embodiment of the reamer 50, head 65 preserves a portion of the anatomic head 2, 64 of the humerus to provide a sufficient bony support and fixation for the humeral implant 10. In another embodiment of the reamer 80, the reamer head 81 which reams into the vault of the humeral metaphysis 5 to allow for new convertible humeral implants 13, 17 (FIGS. 14A, 14B, 14C, 14D).

Each convertible implant 13, 17 comprises an articular humeral component 13a, 17a and a stem 16. The articular humeral component 13a comprises a shell 15 and an articular surface component 18. The articular surface component 18 comprises a convex articulating surface 20 and a coupling surface 29. The articular humeral component 15a comprises the shell 15 and an articular surface component 14. The articular surface component 14 comprises a concave articulating surface 25 and a coupling surface 29. The stem 16 is the same as stem 12a, 12b, except that stem 16 may have a shorter longitudinal length as compared to stem 12a, 12b to account for the space occupied by the shell and portions of the articular humeral component 13a, 17a.

Figure 7:
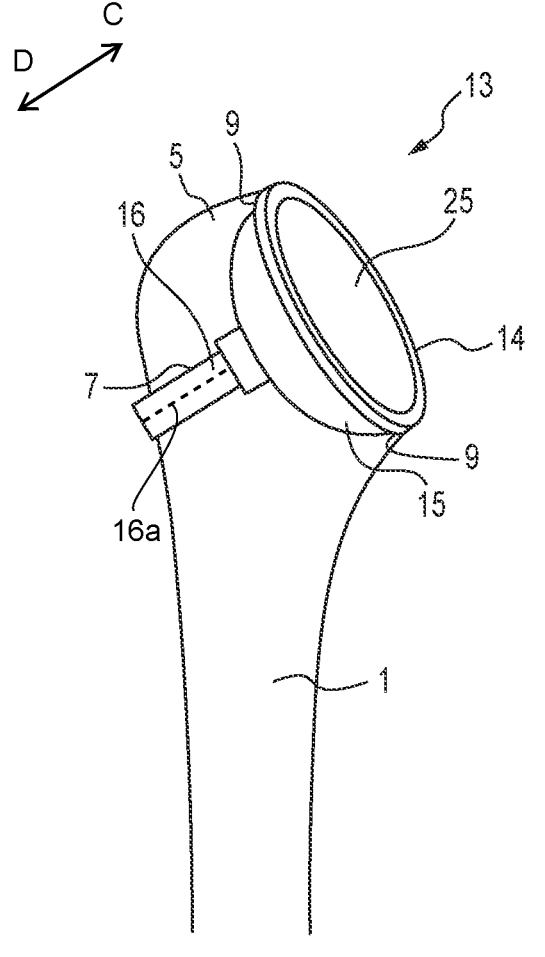
FIG. 7 is a side perspective view of a fourth embodiment humeral implant with a concave articular portion for reverse shoulder arthroplasty.
Figure 8:
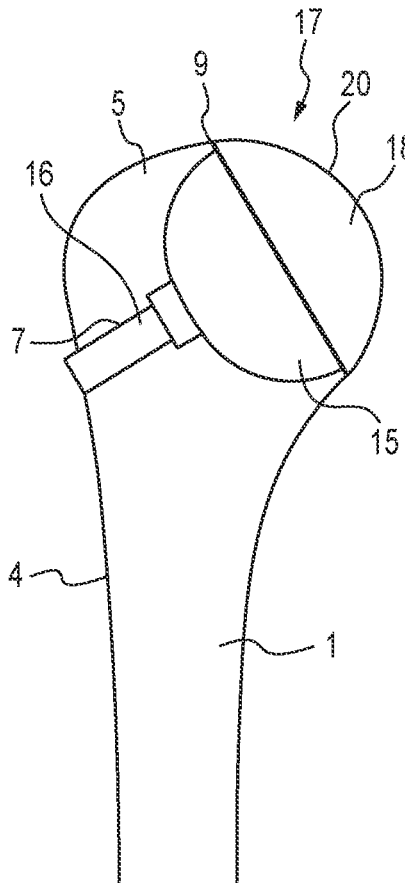
FIG. 8 is a side perspective view the humeral implant of FIG. 7 with a convex humeral articular component for anatomic shoulder arthroplasty.

Implants 13, 17 allow interchangeability of articular surface component 14, 18 with either the convex or concave articulating surface 20, 25 to allow easy conversion between reverse shoulder arthroplasty and anatomic shoulder arthroplasty (FIGS. 7 and 8). The novel convertible humeral implants 13, 17 each use the stem 16 and the shell 15 (9A, 9B, 9C). The articular surface components 14, 18 comprise coupling surfaces 27, 29 that reversibly connect to the coupling surface 28 of the shell 15 (FIGS. 7, 8, 9A, 9B, 9C). The coupling surfaces 27, 29 of the articular portions 14, 18 may possess variable geometry and one of a variety of reversible coupling mechanisms, such as threads. The articular portions 14, 18 may be modular and possess structural voids to reduce weight. The shell 15 may comprise variable protruding geometry with a bony ingrowth surface 21, a peripheral rim 19 to rest upon the prepared cortical rim 9 of the proximal humerus and fins or other prominences 45 extending from the protruding side of the shell 15 (FIGS. 7, 8, 9A, 9B, 9C, 10A, 14D).

Figure 5:
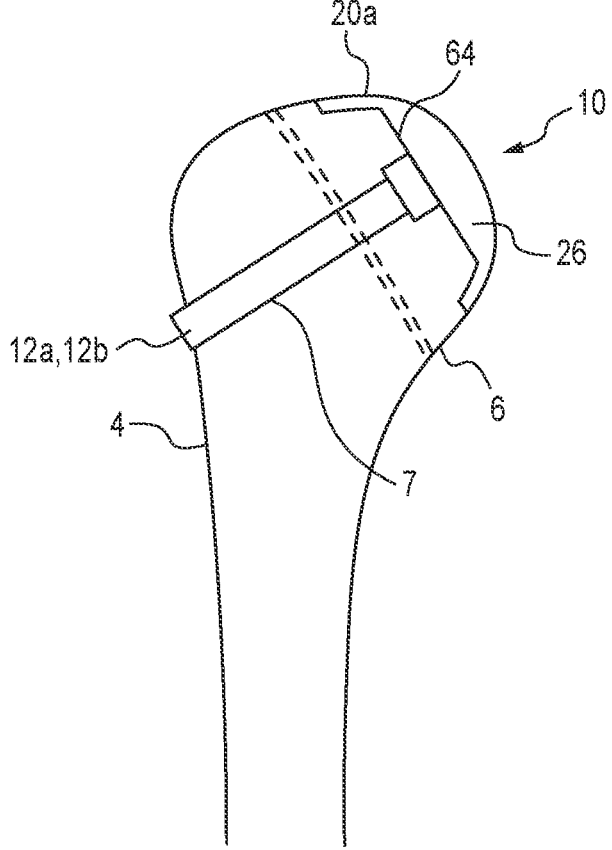
FIG. 5 is side, partially transparent, view a third embodiment of a new humeral implant of the invention having a partial articular component shown in position on a prepared humerus bone.

The stem 12a, 12b, 16 is positioned to reside in the transhumeral tunnel 7 along a central axis of the humeral metaphysis 5 transverse to the plane 6 of the humeral anatomic neck, such as shown in FIGS. 2A, 5 and 7. In some embodiments, the stem 12a, 12b, 16 and the transhumeral tunnel 7 are perpendicular to the plane 6 of the humeral anatomic neck. The stem 12a, 12b, 16 can possess a first end 23 with a coupling feature 23a to engage the opposite coupling feature 22, 22a of the humeral implants 10, 13, 17. In some embodiments, the coupling features 22, 22a, 23a, comprise threads, a press fit, or a Morse taper, or other suitable coupling mechanism to join the stem to the articular component 11, 13a, 17a, 26. It is possible for the male or female counterpart to be on either the stem 12a, 12b, 16 or the articular component 11, 13a, 17a, 26 with the opposite counterpart on the other of the stem 12a, 12b, 16 or the articular component 11, 13a, 17a. In some embodiments, in the case of the coupling feature 22 comprising threads, the coupling feature 22 is a receiver having a peripheral wall surrounding an opening for receiving the stem 12a, 12b, 16, the peripheral wall comprises interior threads for engaging the threads at the first end 23 of the stem. In some embodiments, the stem 12a, 16 comprises a second coupling feature, such as threads or a press-fit, at a second end 24 of the stem opposite the first end as shown for stem 12a in FIG. 3D (not shown for stem 16).

Figure 9A:
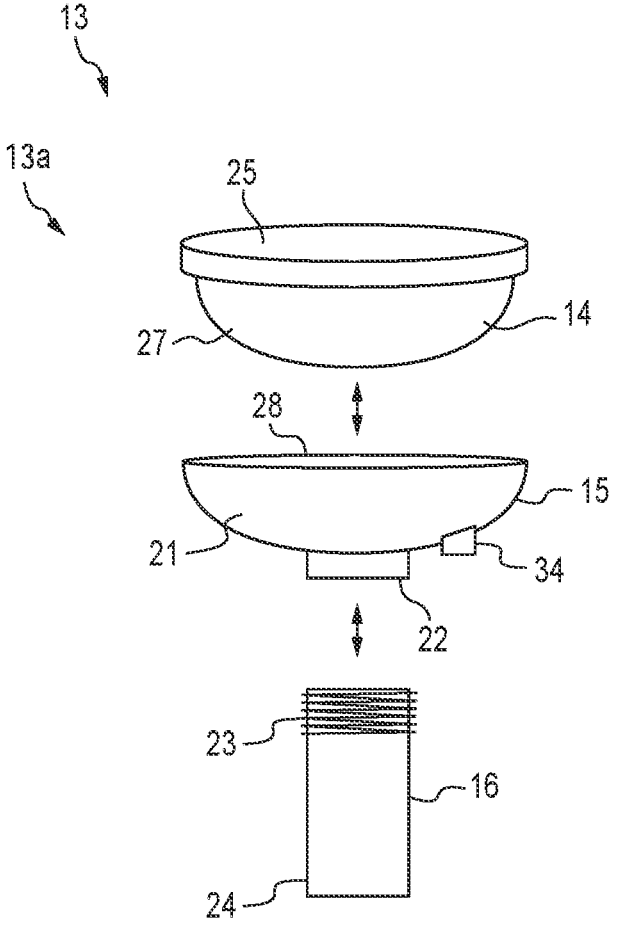
FIG. 9A is an exploded side perspective view of the assembly of the convertible humeral implant of FIG. 7.

In some embodiments, the second end of the stem 12b, 16 does not comprise a second coupling feature but instead may be smooth, such as shown in FIGS. 3E and 9A. The second end of the stem 12a, 12b, 16, whether comprising a second coupling feature or not, obtains contact and stability against the bone of non-articular lateral bony cortex 4 and/or the bone of the humeral metaphysis 5 (FIGS. 2A, 5, 7, 8), when implanted. In various embodiments, the stem may comprise different lengths. In some embodiments, the stem comprises a length such that the stem engages only the bone of the metaphysis 5. In some embodiments, the stem comprises a length such that the stem extends beyond the metaphysis 5 to also engage the non-articular lateral bony cortex 4, and the stem may or may not extend past the lateral end of the lateral bony cortex 4. Therefore, the stem can be contained within the transhumeral tunnel or may extend out of the transhumeral tunnel at the lateral end of the lateral bony cortex 4. In some embodiments, the stem 12a, 12b comprises a length in the range of 1 centimeter (cm) and 12 cm, inclusive. In some embodiments, the stem 16 comprises a length in the range of 1 cm and 6 cm, inclusive. In some embodiments, the stem 12a, 12b, 16 comprises a length that is configured to engage sufficient structural bone of the humerus to resist non-longitudinal displacement of the stem.

In some embodiments and applications, the stem 12a, 12b, 16 also engages a coupling site 31 of the washer-plate 30 on the non-articular lateral bony cortex 4 of the humerus to improve implant stability (FIGS. 6A, 6B, 10A, 10B). In some embodiments, the coupling site 31 comprises threads on a wall of the aperture where the stem is received. Therefore, when the second end 24 of the stem comprise threads, the thread the stem engage the thread of the coupling site 31.

In some embodiment and applications, the stems 12a, 12b, 16 are configured for slidable engagement with the non-articular lateral bony cortex 4 of the humerus, the washer-plate 30, and/or the bone of the humeral metaphysis 5 to allow more physiologic load transmission of joint compressive forces to the remainder of the bone of the humerus 1 through the humeral implants 10, 13, 17. The stem 12a, 12b 16 is configured not to be axially fixed within the transhumeral tunnel, but instead to slide within the transhumeral tunnel 7, including after implantation surgery is complete, i.e. post-surgery. The stem can slide longitudinally within the transhumeral tunnel 7 and axially along a longitudinal axis 12c, 16a of the stem, in the directions A and B of FIG. 2A and directions C and D of FIG. 7. The stem 12a, 12b 16 can be limited in its sliding range of motion in the first direction B, D, at the first end 23 by the articular component 11, 13a, 17a engagement with the humeral head. The stem does not axially shelter the load borne by the articular component from the surrounding proximal humeral bone in direction B, D. This non-load-sheltering aspect of the stem contributes to more physiologic load transmission of joint compressive forces to the remainder of the bone of the humerus 1 through the humeral implants 10, 13, 17. In some embodiments, the width or diameter of the stem 12a, 12b, 16 less than the width or diameter of the transhumeral tunnel 7 and therefore stem does not friction fit against the wall(s) of the transhumeral tunnel 7 and therefore the stem is slidable within the transhumeral tunnel 7, including post-surgery. In some embodiments, the stem 12a, 12b, 16 can be provided with a smooth exterior, such as a smooth exterior surface below the coupling feature 23a at the first end 23 of the stems shown in FIGS. 3E and 9A. And, at least the second end 24 may be smooth, such as shown in FIGS. 3E and 9A. The stem 12a, 12b, 16 may comprise a non-bone-adherent surface. The stem 12a, 12b, 16 may comprise a non-bone-adherent coating on an exterior surface of the stem. In some embodiments, the stem has a uniform width and cross-section along the longitudinal length of the stem or a portion thereof.

In some embodiments, the second end 24 of the stem 12a, 12b, 16 is enlarged to prevent movement toward the articular component in the direction A, C, where the enlarged portion engages with a portion of the tunnel 7, which is narrower than the enlarged portion, at least in part, to prevent further movement in the direction A, C. In some embodiments, the stem 12a, 12b, 16 comprises ridges, fins, and/or unidirectional ridges and these features of the stem do not limit movement of the stem away from the articular component along its axis, such as in the direction B, D. In some embodiments, the stem 12a, 12b, 16 may be considered nonadherent within the tunnel 7 in that they allow movement away from the articular component, such as in the direction B, D. The range of movement in a first direction of the stem within the tunnel may be limited by the articular components' engagement with the prepared portion of a proximal humerus via the connection between the stem and the articular components. In some embodiments, the range of movement of the stem in a second direction, opposite the first direction, in the tunnel 7 may be limited by an enlarged second end 24 of the stem and its engagement with the tunnel or another fixture.

Figures 6A, 6B:
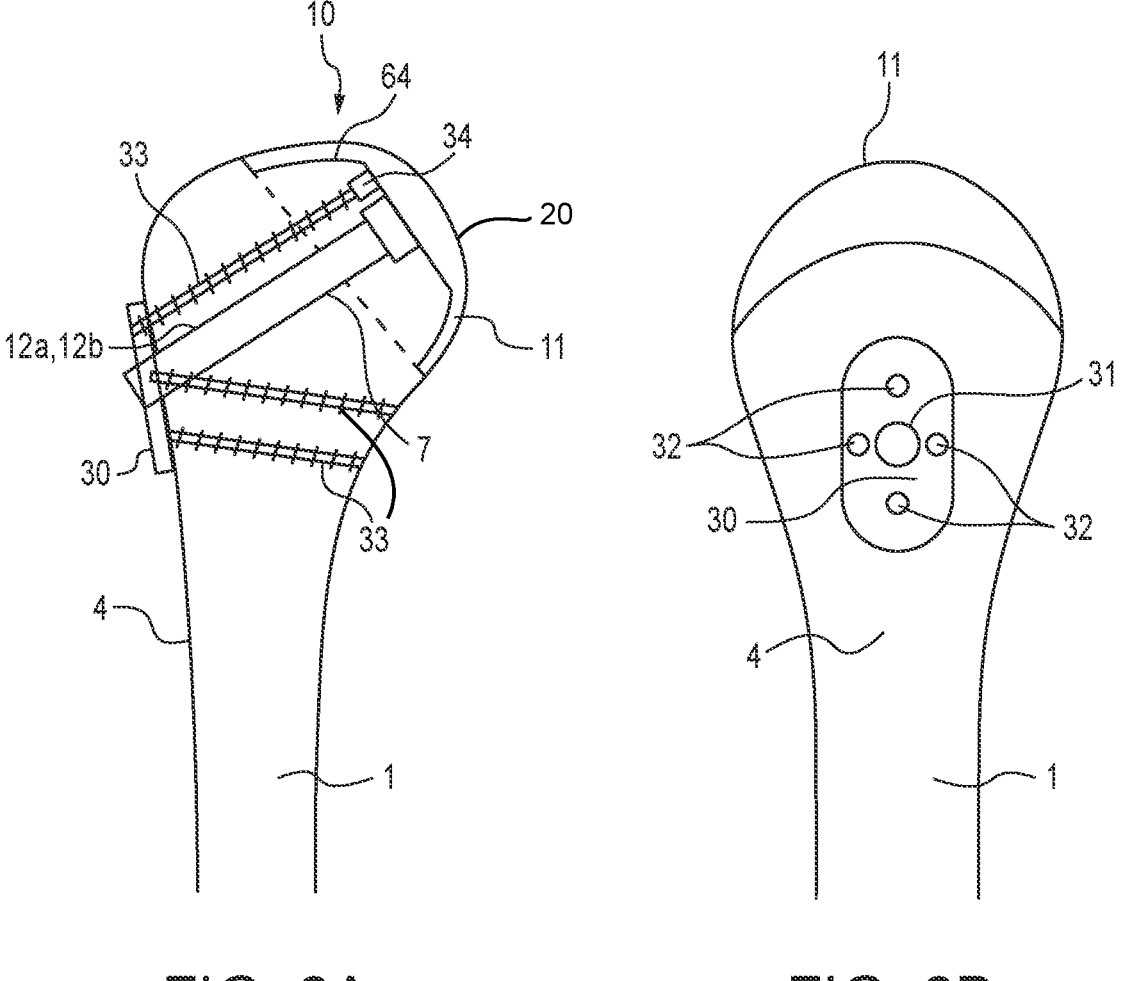
FIG. 6A is a side view of a humeral implant of FIG. 3A with an associated lateral buttress plate secured to the bone with screws engaging the implant with a stem.
FIG. 6B is a second view of the humeral implant of FIG. 6A with an associated lateral buttress plate secured to the bone with screws and/or screws engaging the implant and the lateral buttress plate.

In some embodiments, the washer-plate 30 does not have a coupling site and instead a nut (not shown) is fixed to the threaded second end 24 of the stem 12a, 12b, 16 after the plate (e.g. to the left of the plate in FIG. 6A). In such embodiments, the stem, by not being fixed to the plate, the non-articular lateral bony cortex 4, or the perimeter of the transhumeral tunnel 7, the stem is allowed movement along the axis of the stem within a range bounded by the nut. The nut limits the range of movement, in the second direction, away from the non-articular lateral bony cortex 4 and toward articular humeral component 11 or shell 15, but not towards the non-articular lateral bony cortex 4.

Alternatively, the stems 12a, 12b, 16 can capture either the non-articular lateral bony cortex 4 of the humerus or an optional washer-plate 30 and the articular humeral component 11 or the shell 15 of the humeral implants 10, 13, 17, serving to compress them together against the intervening elements of humeral bone 3, 4, 5 (FIGS. 3D, 6A, 6B, 10A, 10B). In some embodiments, screws 33 can be used through cannulations 32 to help secure the washer-plate 30 to the non-articular lateral bony cortex 4 of the humerus (FIGS. 6A, 10A). The screws 33 can be used to compress the washer-plate 30 against lateral bony cortex 4 of the humerus 1 or can be fixed angle and locking to achieve rigid fixation to the humerus bone 1. Additional screws 33 can also bridge between cannulations 32 in the washer-plate 30 and screw optional coupling sites 34 of the humeral implants 10,13,17.

The portions of the shell 15 and the articular humeral components 11, 26 that interface with the bone may have a suitable protruding bony ingrowth surface(s) 21 to allow long-lasting adhesion to the humeral head 2 and metaphysis bone 5. Each stem 12a, 12b, 16 has two ends 23, 24 (FIGS. 3D and 3E). One end 23 removably attaches to the coupling device 22 of the shell 15 or the articular humeral components 11, 26 and another end 24 which engages the non-articular lateral bony cortex 4 of the humerus or the coupling site 31 of an optional washer-plate 30 fixed to the non-articular lateral bony cortex 4 of the humerus, or a nut, as explained above. In some embodiments, the remainder of the stem 12a, 12b, 16 may possess a bone ingrowth surface but ideally would not to facilitate slidable engagement and removal as necessary. Alternatively, the end 24 of the stem 12a, 12b,16 may be smooth and allow slidable contact with the lateral washer-plate 30, the non-articular lateral bony cortex 4 and/or transhumeral tunnel 7 along a central axis in the metaphysis 5 of the humerus 1, as more fully explained above.

Figure 11A:
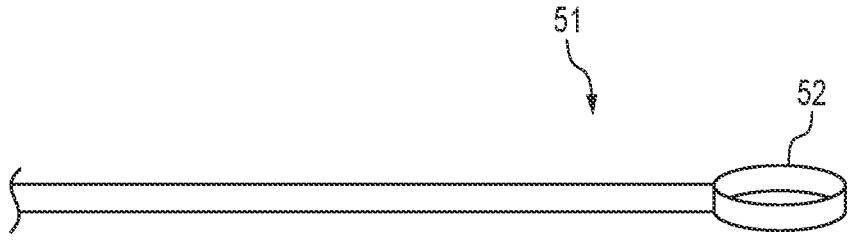
FIG. 11A is a perspective view of a handle arranged to hold the head of a new humeral reamer.
Figure 11B:
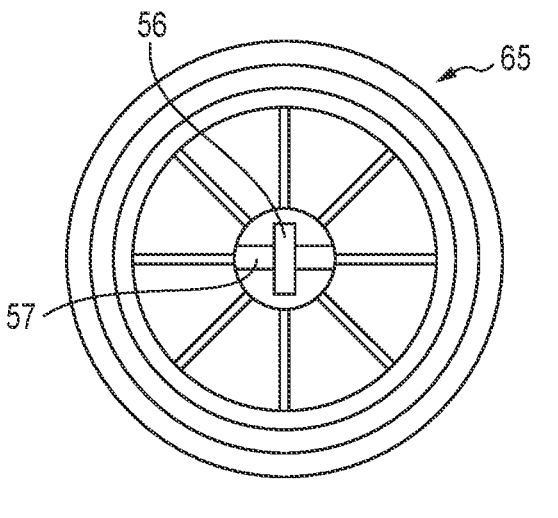
FIG. 11B is a top view of the head of the new humeral reamer that interacts with the handle of FIG. 11A.
Figure 11C:
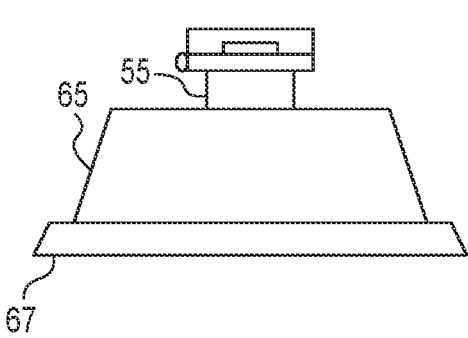
FIG. 11C is an elevational view of the head of the new humeral reamer that interacts with the handle of FIG. 11A.
Figure 11D:
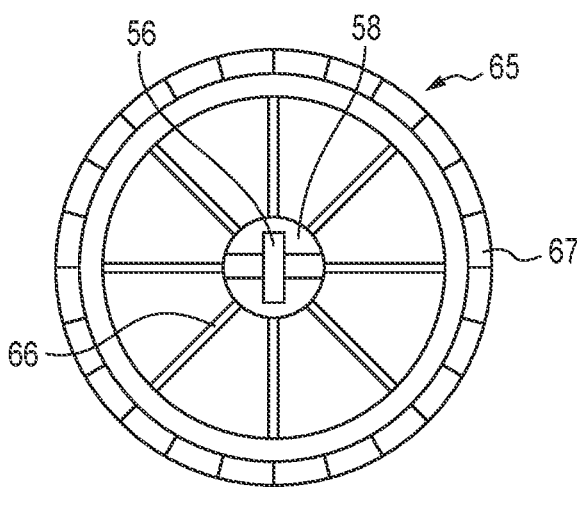
FIG. 11D is a bottom view of the head of the new humeral reamer and of FIGS. 11B and C.
Figure 11E:
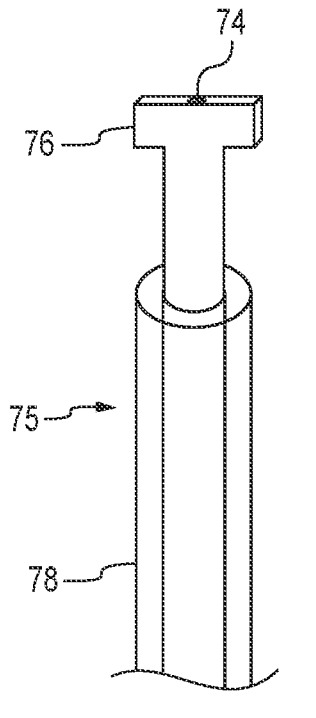
FIG. 11E is a side view of a portion of the shaft with engagement tip of the shaft and centering handle sleeve to interact with the head of the new humeral reamer of FIGS. 11B, 11C, and 11D.
Figure 12A:
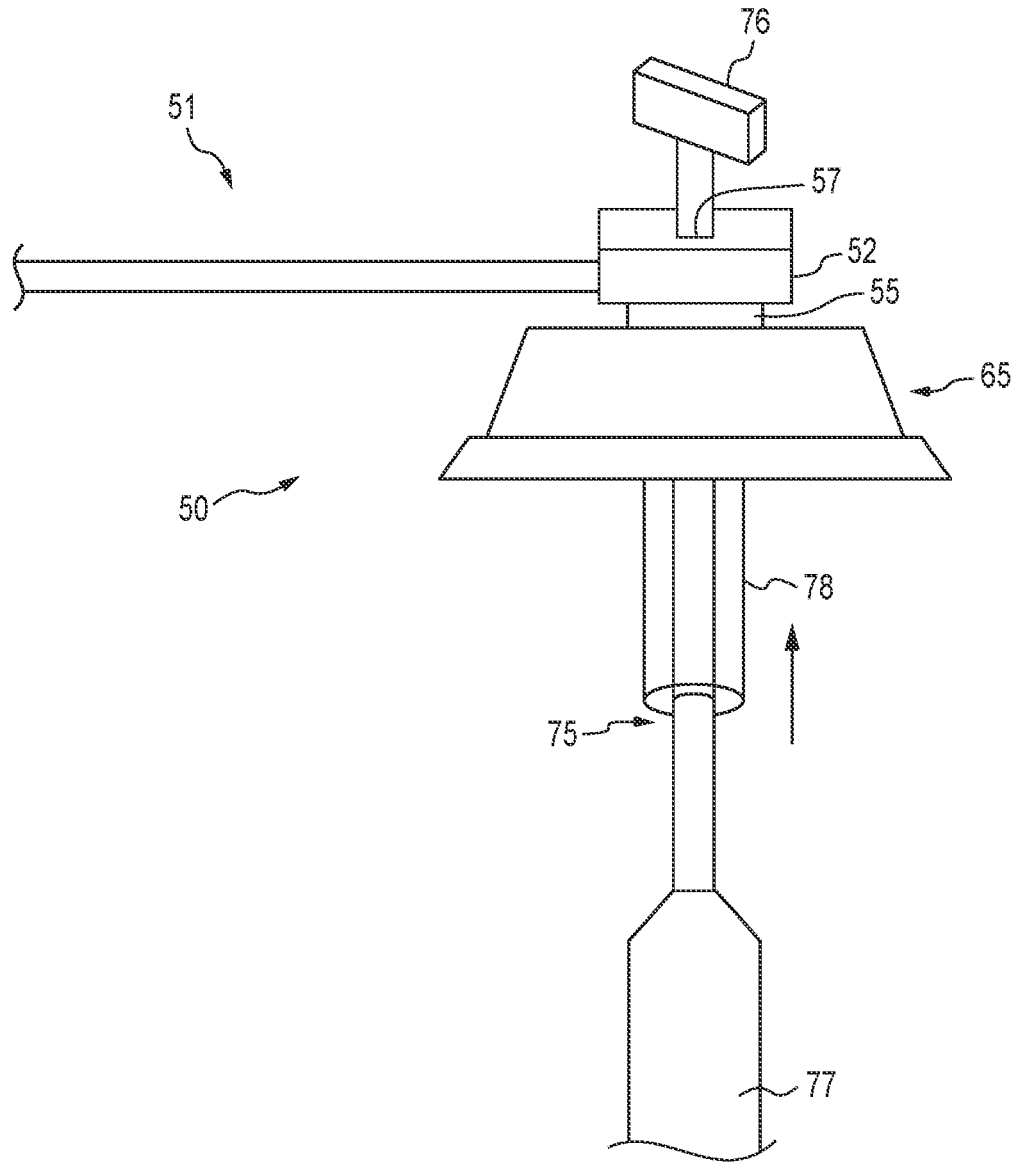
FIG. 12A is a side view of the humeral reamer and shaft preliminarily arranged to be reversibly engaged to each other.
Figure 12B:
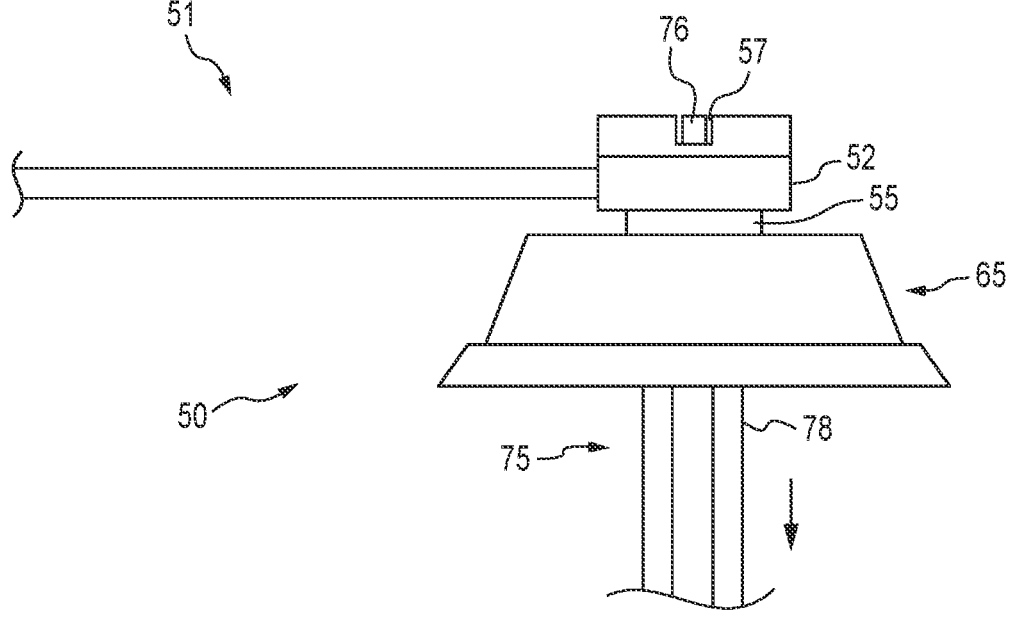
FIG. 12B is a side view of the humeral reamer and shaft of FIG. 12A reversibly engaged to each other.
Figure 14A:
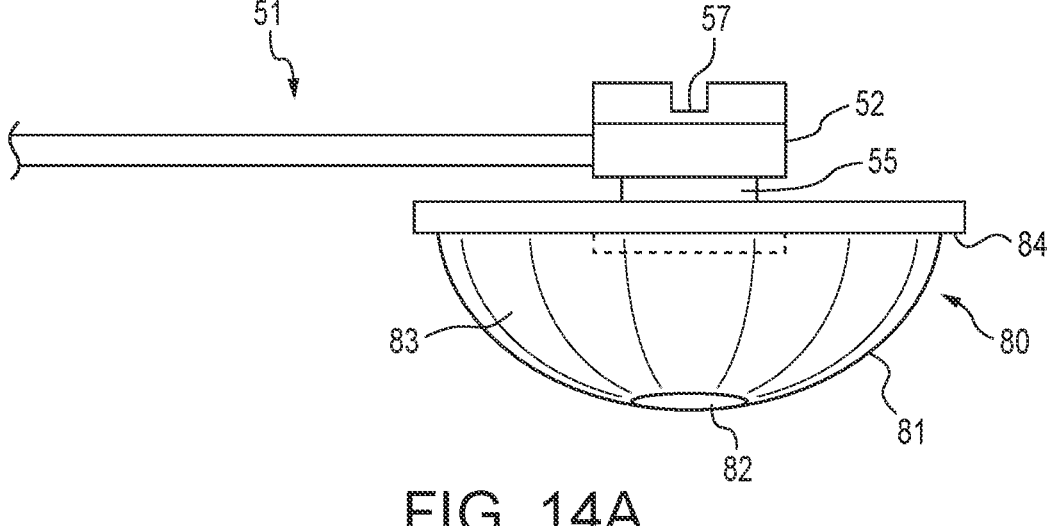
FIG. 14A is a side view of the humeral reamer and handle to prepare a humerus for the installation of a new convertible humeral implant.
Figure 14B:
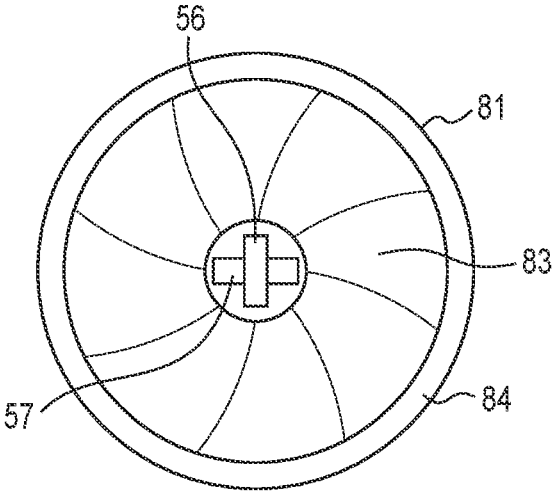
FIG. 14B is a bottom view of the humeral reamer of FIG. 14A.
Figure 14C:
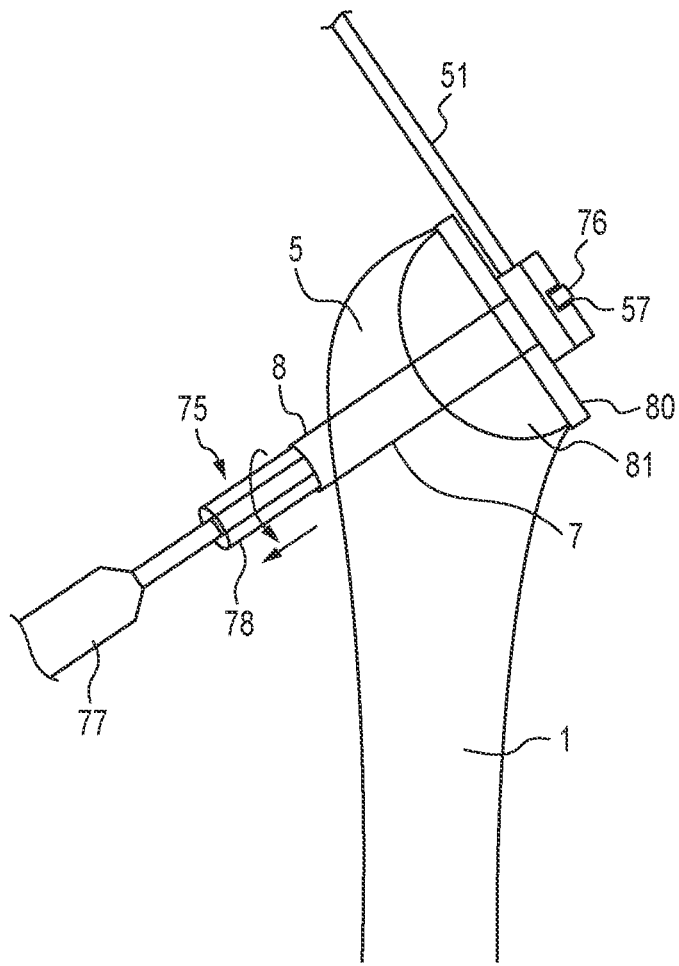
FIG. 14C is a perspective view of the humeral reamer of FIG. 14A and shaft of FIG. 11E arranged through a transhumeral passage in the humerus for a step to prepare a humerus for the installation of the new convertible humeral implant.
Figure 14D:
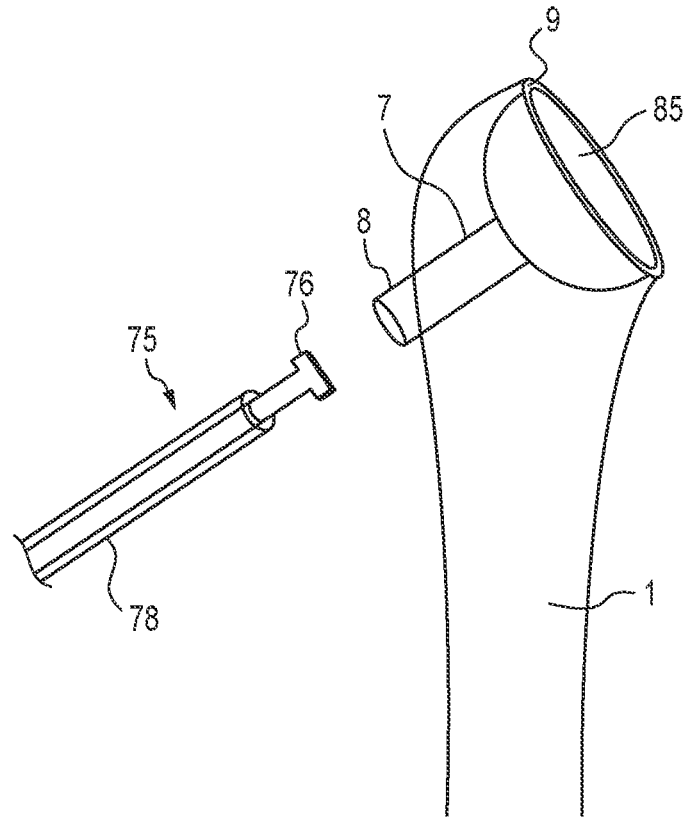
FIG. 14D is a perspective view of the prepared humerus and transhumeral sheath after steps to prepare the humerus for the installation of the new convertible humeral implant where the reamer shaft and head of FIG. 14C are disengaged and removed.
Figure 15A:
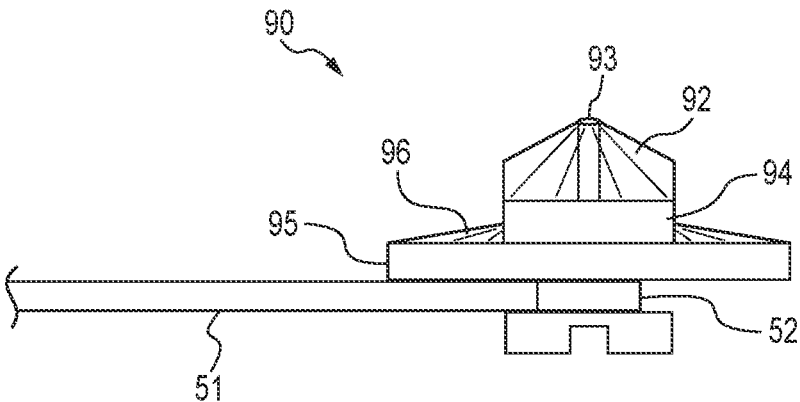
FIG. 15A is an elevational view of the new modular glenoid reamer and handle.
Figure 15B:
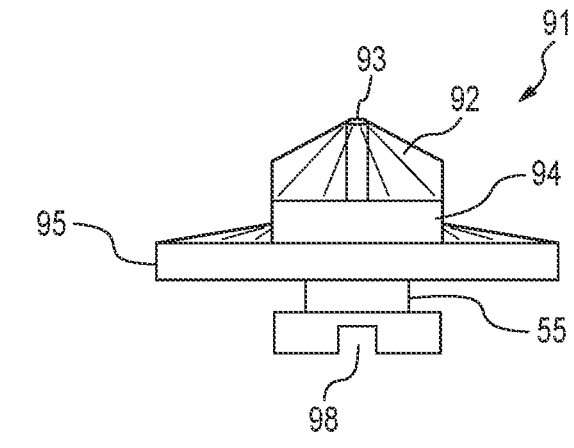
FIG. 15B is a second elevational view of the new modular glenoid reamer of FIG. 15A.
Figure 15C:
FIG. 15C is a side perspective view of a handle arranged to hold the head of the new glenoid reamer of FIG. 15A.

In some embodiments, modular transhumeral reamers 50, 80, 90 are utilized to prepare the humeral and glenoid surfaces 3, 42 for novel implant application (FIGS. 12A, 14A, 15A). Reamer 50, 80, 90 comprises a cutting reamer head 65, 81, 91 with an axle 55, a central cannulation 56, 93, and a handle 51 (FIGS. 11A, 11B, 11C, 11D, 11E, 14A, 14B, 15A, 15, 15B, 15C). The handle 51 has a ring end 52 which captures the axle 55 and allows the axle 55 and the reamer head 65, 81, 91 to spin freely in the ring end 52. The reamer head 65, 81, 91 has a surface configured for bone drilling or cutting 66, 67, 83, 92, 96 and a slot 57, 98, opposite the cutting or drilling surface configured for temporary engagement with the tip 76 of the transhumeral reamer shaft 75. The shaft 75 of the reamers 50, 80, 90 can be driven by hand or a power drill 77.

Figure 16A:
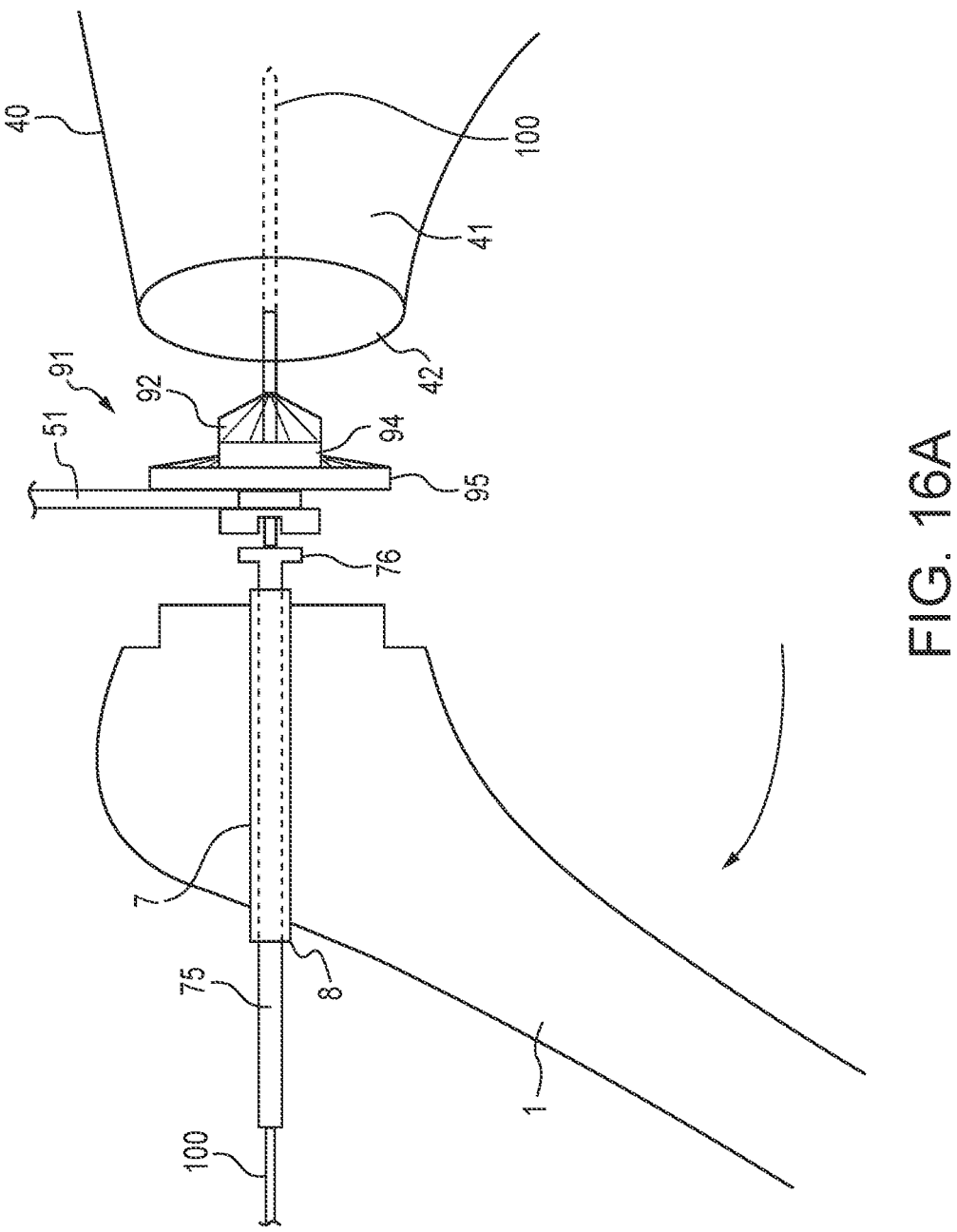
FIG. 16A is a perspective view of the glenoid reamer of FIG. 15A and shaft of FIG. 11E arranged through a transhumeral passage in a humerus to prepare the glenoid for a glenoid implant.
Figure 16B:
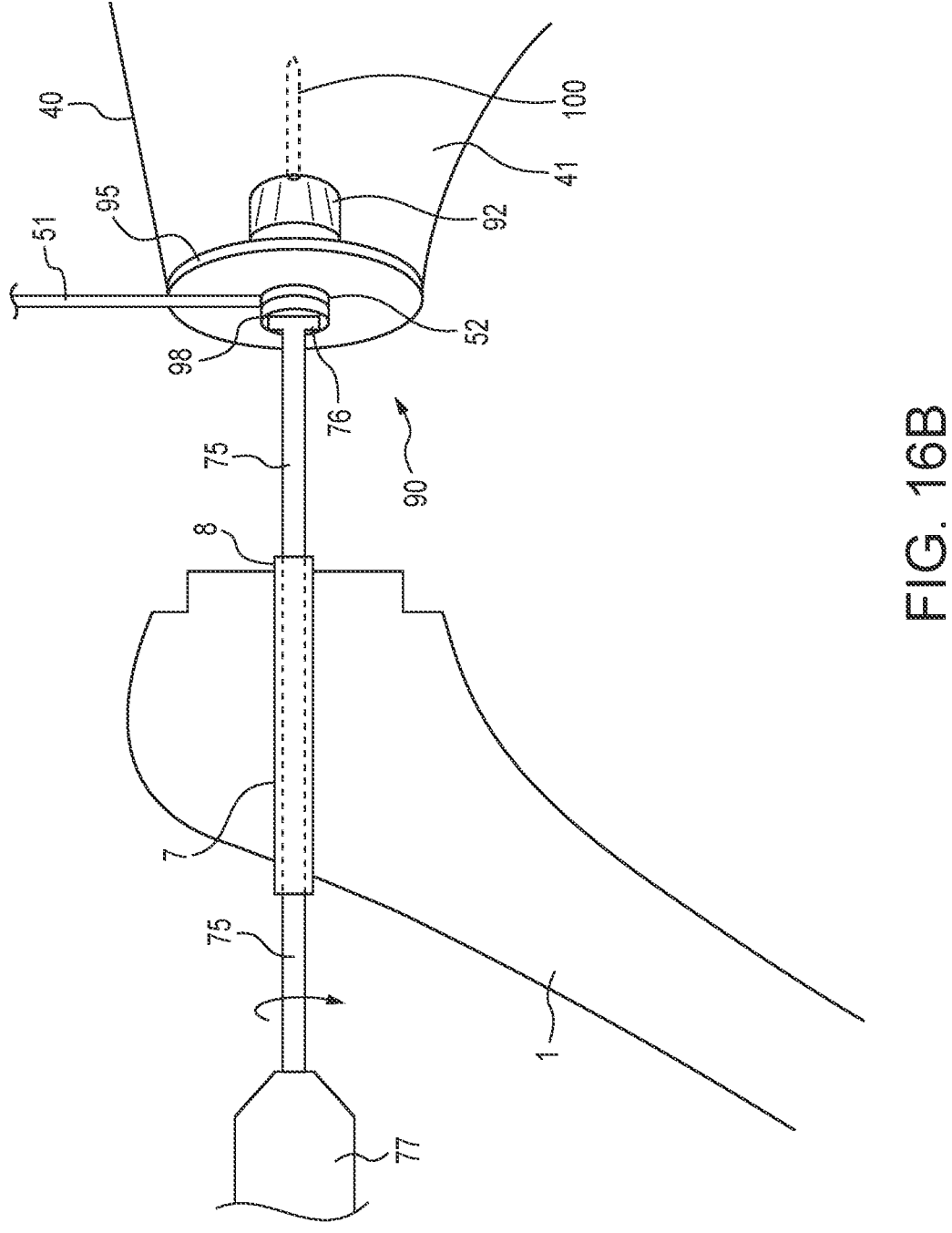
FIG. 16B is a second perspective view of the glenoid reamer and shaft of FIG. 16A arranged through a transhumeral passage in a humerus to prepare the glenoid for a glenoid implant.
Figure 16C:
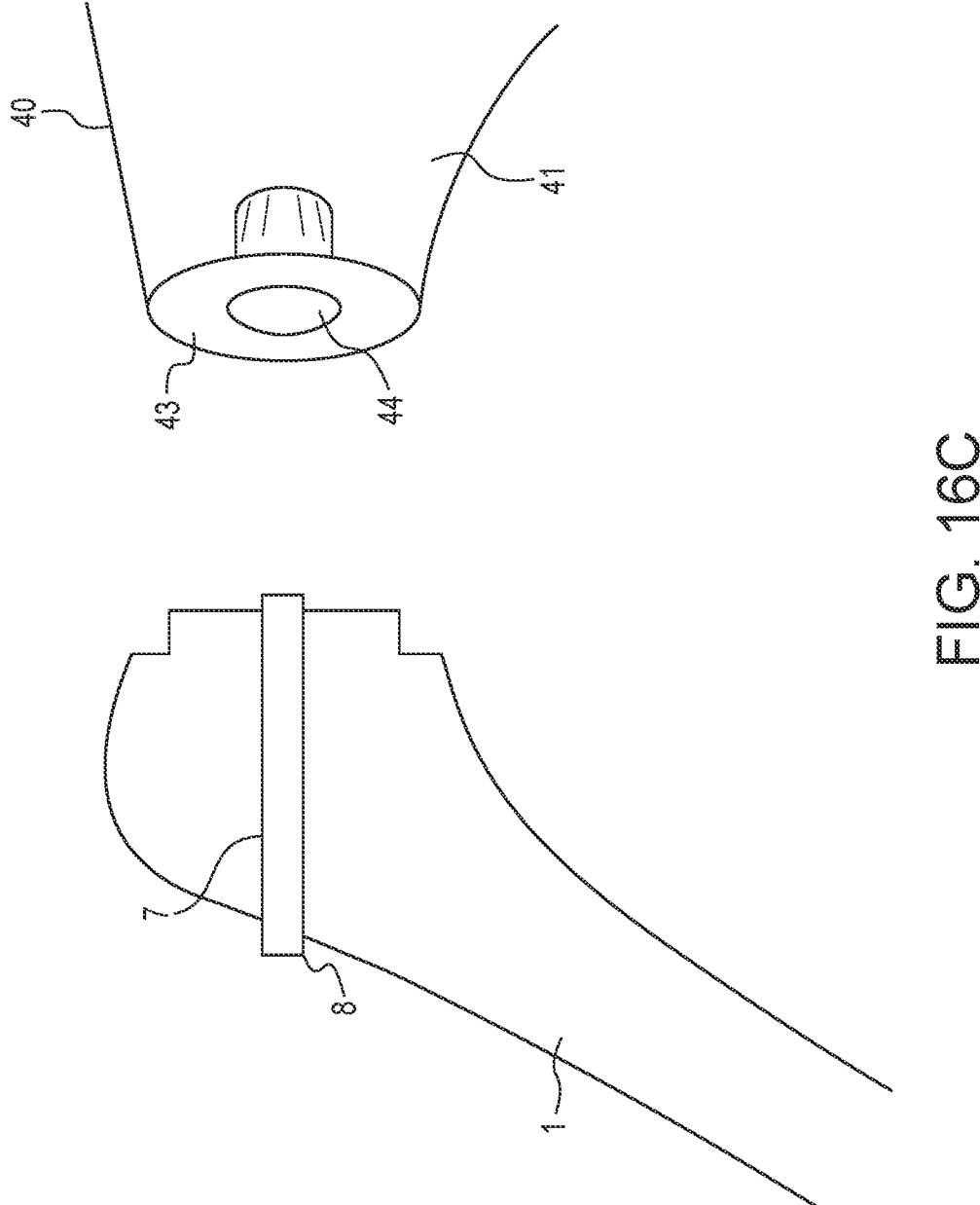
FIG. 16C is a third perspective view of the humerus and glenoid of 16A after the glenoid and humerus have been prepared by humeral and glenoid reamers of FIGS. 13A and 16A through a transhumeral passage in the humerus.

The reamers 50, 80, 90 are modular and may be used through open surgical approaches used for traditional open shoulder arthroplasty surgery or they can be used for minimally invasive rotator cuff sparing shoulder arthroplasty surgery through a transhumeral tunnel 7 approach which spares the rotator cuff, preserves humeral bone, and avoids dislocation of the shoulder joint associated with traditional approaches. For the transhumeral approach, the reamers 50, 80, 90 are inserted by their handle 51 through a non-bony passageway, likely an interval in the rotator cuff, and into position in the shoulder joint while the transhumeral reamer shaft 75 is inserted through the transhumeral tunnel 7 and an optional protective transhumeral sheath 8 into the shoulder joint and reversibly coupled by the engagement tip 76 to the engagement slots 57, 98 of the reamer 50, 80, 90 (FIGS. 13A, 13 B, 13C, 13D, 14C, 14D, 16A, 16B, 16C). The reamer 50, 80, 90 can be configured to be used to drill and cut transverse or perpendicular to the axis of the reamer shaft 75, particularly not off-axis. For example, the cut surfaces 65*a, b, c*, of the prepared portion of humeral head shown in FIG. 13D after the use of the reamer in FIGS. 13B and 13C shows that the reamer can cut planes that are perpendicular to the axis of the reamer shaft 75. There is a centering sleeve 78 moving freely around the reamer shaft 75 that engages a centering cannulation 58, 82 on the reamer heads 65, 81 to ensure the reamer cuts the humeral surface 3 on axis, i.e perpendicular to the transhumeral tunnel 7 and the reamer shaft 75. The glenoid reamer 90 does not require a centering sleeve 78 but rather is cannulated 93 to ream over a guide pin 100 positioned through the transhumeral tunnel 7 and the protective transhumeral sheath 8 and into the surface 42 and vault 41 of the glenoid 40 (FIGS. 16A, 16B, 16C). The reamer shaft for the glenoid also possesses a cannulation 74 for the guide pin 100.

The cutting surfaces 66, 67, 83, 84, 92, and 96 vary in geometry and aggressiveness to optimally prepare the bone 3, 5, 41, 42 for their respective implants 10, 13, 17. The reamer head 65 has two cutting surfaces 66, 67, one cutting surface 66 to cut the humeral surface 3 and the other cutting surface 67 to cut the perimeter to the level 6 of the anatomic neck of the humerus 1 (FIG. 11D). The reamer head 81 for the convertible humeral implant 13,17 also has two cutting surfaces, one protruding cutting surface 83 with variable geometry to cut a humeral metaphyseal socket 85 and a second 84 to cut the perimeter near the level 6 of the anatomic neck of the humerus 1 (FIGS. 14A, 14B). The cutting surface 92, 96 of the glenoid reamer 90 has a protruding aggressive cutting surface 92 to cut a precise glenoid cavity 44 into the glenoid vault 41; an intermediate smooth non-cutting surface 94 to help keep the reamer 90 on axis and prevent damage to prepared peripheral glenoid surface bone 43; and a less aggressive cutting surface 96 on the peripheral rim 95 of the glenoid reamer head 91 to less aggressively prepare the peripheral aspect of the glenoid surface 42 (FIGS. 16A, 16B, 16C).

In some embodiments, the implants 10, 13, 17 can be implanted through an implant method that comprises the following steps: fixing an articular humeral component 11, 26, 13*a*, 17*a* comprising an articular surface 20, 25 to a prepared articular portion of a proximal humerus; placing a stem 12*a*, 12*b*, 16 in the tunnel 7 in the proximal humerus without fixing the stem within the tunnel 7; and, connecting the stem to the articular humeral component. Depending on the chosen approach for implantation, the order of the foregoing steps can vary. Further, in some embodiments, the connecting step is not used, for example, when the stem is already fixed to or formed with the articular humeral component.

In some embodiments, the step of connecting occurs before the articular humeral component is fixed to the proximal humerus, and in some cases, before the stem is placed in the tunnel 7. For example, when the stem and the articular humeral component are implanted as a unit, the stem being placed from the articular side of the humerus into the tunnel 7 toward the lateral bony cortex 4, in the direction D, B. The stem being moved into the tunnel until the articular humeral component is seated on the prepared articular portion. The articular humeral component may be fixed at or after the humeral component is seated on the prepared articular portion.

In some embodiments, the stem is placed through tunnel 7 from the lateral bony cortex 4 side in the direction A, C and is connected to the articular humeral component before the articular humeral component is fixed to the prepared articular portion of a proximal humerus. In some embodiments, the stem is placed in the tunnel, the articular humeral component is fixed to the prepared articular portion of a proximal humerus, and then the stem is connected to the articular humeral component.

In some embodiments, the step of connecting occurs during the step of placing. For example, the stem may be connected articular humeral component when it is placed within the tunnel. As explained above, in some embodiments, the stem is placed in the tunnel 7 in the proximal humerus without fixing the stem within the tunnel against post-surgery longitudinal movement.

It is therefore intended that the foregoing detailed description be regarded as illustrative rather than limiting, and that it be understood that it is the following claims, including all equivalents, that are intended to define the spirit and scope of this invention.

The invention claimed is:

1. A humeral implant comprising:
   an articular humeral component comprising an articular surface and configured for fixation to an articular portion of a proximal humerus; and
   a non-bone-adherent stem connected to the articular humeral component and configured for post-surgery axial sliding contact with a bone wall of a tunnel within the humerus to stabilize the stem against non-axial displacement and to prevent the stem from bearing a load from the articular humeral component applied in an axial direction.

2. The humeral implant of claim 1, wherein the stem comprises a non-bone-adherent coating on an exterior surface of the stem.

3. The humeral implant of claim 1, wherein the stem comprises a length sufficient to traverse a non-articular lateral bony cortex of the humerus opposite the articular portion.

4. The humeral implant of claim 1, wherein the articular humeral component comprises a bone fixation component and an articular surface component, the stem is removably connected to the bone fixation component, the bone fixation component is removably connected to the articular surface component, and the articular surface component comprises the articular surface.

5. The humeral implant of claim 1, wherein the stem comprises a cylindrical shape.

6. The humeral implant of claim 1, wherein the stem is removably connected to the articular humeral component.

7. The humeral implant of claim 1, wherein the stem is permanently connected to the articular humeral component.

8. The humeral implant of claim 1, wherein the articular humeral component comprises a bone fixation component, and the bone fixation component comprises a fastener coupling.

9. The humeral implant of claim 8, comprising a screw received in the fastener coupling.

10. The humeral implant of claim 1, comprising a washer plate for engaging a lateral non-articular bone surface of the humerus, the washer plate configured to receive the stem.

11. The humeral implant of claim 10, wherein the stem is axially slidably received by the washer plate.

12. The humeral implant of claim 1, wherein the stem is configured to extend along a central axis of a neck of the humerus.

13. A humeral implant comprising:

an articular humeral component comprising an articular surface and configured for fixation to an articular portion of a proximal humerus; and an axially non-load-sheltering stem configured for post-surgery contact with a bone wall of a tunnel within the humerus to stabilize the stem against non-axial displacement, the stem connected to a side of the articular humeral component configured to face the proximal humerus, the stem comprising a non-bone-adherent surface.

14. The implant of claim 13, wherein the non-bone-adherent surface comprises a non-bone-adherent coating.

15. The implant of claim 1, wherein the articular humeral component comprises an at least one bone fixation surface configured to transfer the load from the articular humeral component applied in the axial direction to the articular portion of the proximal humerus.

16. The implant of claim 15, wherein the articular humeral component comprises an articular side and a fixation side, the articular surface is on the articular side and the bone fixation surface is on the fixation side;

the bone fixation surface is interrupted by a connection of the stem to the fixation side; and, the stem comprises a non-bone-adherent coating.

17. The implant of claim 13, wherein the stem comprises a uniform cross-section along a longitudinal length of the stem.

* * * * *